(12) United States Patent
Pumerantz et al.

(10) Patent No.: US 9,566,238 B2
(45) Date of Patent: Feb. 14, 2017

(54) FORMULATION OF PEGYLATED-LIPOSOME ENCAPSULATED GLYCOPEPTIDE ANTIBIOTICS

(75) Inventors: Andrew Pumerantz, Irvine, CA (US); Guru Betageri, Chino Hills, CA (US); Jeffrey Jinghua Wang, Arcadia, CA (US)

(73) Assignee: WESTERN UNIVERSITY OF HEALTH SCIENCES, Pomona, CA (US)

(*) Notice: Subject to any disclaimer, the term of this patent is extended or adjusted under 35 U.S.C. 154(b) by 90 days.

(21) Appl. No.: 13/805,027

(22) PCT Filed: Jun. 20, 2011

(86) PCT No.: PCT/US2011/041053
§ 371 (c)(1),
(2), (4) Date: Mar. 13, 2013

(87) PCT Pub. No.: WO2011/160110
PCT Pub. Date: Dec. 22, 2011

(65) Prior Publication Data
US 2013/0164370 A1 Jun. 27, 2013

Related U.S. Application Data

(60) Provisional application No. 61/356,601, filed on Jun. 19, 2010.

(51) Int. Cl.
*A61K 9/127* (2006.01)
*A61K 38/14* (2006.01)
*C07K 9/00* (2006.01)

(52) U.S. Cl.
CPC ............. *A61K 9/1271* (2013.01); *A61K 38/14* (2013.01); *C07K 9/008* (2013.01)

(58) Field of Classification Search
None
See application file for complete search history.

(56) References Cited

U.S. PATENT DOCUMENTS

| 5,843,473 A * | 12/1998 | Woodle ................ C07F 9/5537 424/450 |
| 2005/0118250 A1 | 6/2005 | Tardi et al. |
| 2007/0014845 A1* | 1/2007 | Zhang et al. .................. 424/450 |
| 2007/0110798 A1* | 5/2007 | Drummond et al. .......... 424/450 |
| 2009/0104257 A1* | 4/2009 | Li et al. ........................ 424/450 |

FOREIGN PATENT DOCUMENTS

| CN | 1717220 A | 1/2006 |
| JP | H06345663 A | 12/1994 |
| JP | H10001431 A | 1/1998 |
| JP | 2006508126 A | 3/2006 |
| JP | 2007500239 A | 1/2007 |
| JP | 2007536247 A | 12/2007 |
| JP | 2008515929 A | 5/2008 |
| WO | 9105546 A1 | 5/1991 |
| WO | 98/16202 A2 | 4/1998 |
| WO | 03/041681 A2 | 5/2003 |
| WO | 2004/043363 A2 | 5/2004 |
| WO | 2004043363 A2 | 5/2004 |
| WO | 2004/047802 A2 | 10/2004 |
| WO | 2005107712 A1 | 11/2005 |
| WO | 2006/042270 A1 | 4/2006 |
| WO | 2007/121947 A1 | 11/2007 |
| WO | 2009/044406 A2 | 4/2009 |
| WO | 2009/142892 A1 | 11/2009 |
| WO | 2011/160110 A1 | 12/2011 |

OTHER PUBLICATIONS

PCT International Search Report and Written Opinion for PCT International Application PCT/US2011/041053 dated Oct. 25, 2011.
Mu et al., "Vancomycin disulfide derivatives as antibacterial agents", Bioorganic & Medicinal Chemistry Letters, 2004, vol. 14, Iss. 2, pp. 735-738.
Sheetz et al., "Potential Impact of Vancomycin Pulmonary Distribution on Treatment Outcomes in Patients with Methicillin-Resistant *Staphylococcus aureus* Pneumonia", Pharmacotherapy, Nov. 4, 2006, vol. 26, Iss. 4, pp. 539-550.
Pumerantz et al., "Preparation of liposomal vancomycin and intracellular killing of meticillin-resistant *Staphylococus aureus* (MRSA)", International Journal of Antimicrobial Agents, Dec. 3, 2010; vol. 37, Iss. 2, pp. 140-144.
Immordino, ML, et al. Stealth liposomes: review of the basic science, rationale, and clinical applications, existing and potentials, International Journal of Nanomedicine. vol. 1, No. 3, pp. 297-315. Sep. 2006.
International Preliminary Report on Patentability for PCT International Application No. PCT/US2011/041053, dated Dec. 19, 2012.
Extended European Search Report for EP Application No. 11796573.1, dated Nov. 13, 2013.

(Continued)

*Primary Examiner* — Frederick Krass
*Assistant Examiner* — Celeste A Roney
(74) *Attorney, Agent, or Firm* — A. Lindeman & Co., PLLC

(57) ABSTRACT

This invention is directed to a novel method of treating an individual suffering from a bacterial infection, such as bacterial infections of various tissues or organs of an individual. In general, the method of treatment involves administering to an individual a pharmaceutical formulation that comprises a liposome-encapsulated antimicrobial agent, wherein polyethylene glycol (PEG) molecules are covalently attached to the surface of the liposomes.

19 Claims, 5 Drawing Sheets

(56) References Cited

OTHER PUBLICATIONS

P. Deol et al., "Lung Specific Stealth Liposomes: Stability, Biodistribution and Toxicity of Liposomal Antitubercular Drugs in Mice," Biochemica et Biophysica Acta, 1997, 1334, pp. 161-172.
Office Action from Japanese Patent Application No. 2013-516651, dated Feb. 13, 2015 (English translation).
English Language Abstract of JPH06345663A.

\* cited by examiner

FORMULATION OF PEGYLATED-LIPOSOME ENCAPSULATED GLYCOPEPTIDE ANTIBIOTICS

CROSS REFERENCE TO RELATED APPLICATION

This application claims benefit of priority of PCT International Application No. PCT/US2011/041053, filed Jun. 20, 2011; which claims priority to U.S. Provisional Patent Application No. 61/356,601 filed on Jun. 19, 2010, the entire disclosures of which are incorporated herein by reference.

FIELD OF THE INVENTION

This invention relates to liposome-mediated delivery of pharmaceutical agents.

BACKGROUND OF THE INVENTION

Methicillin-resistant *Staphylococcus aureus* (MRSA) is a bacterium that causes over half the cases of hospital-acquired pneumonia (1-3). It may also be referred to as multidrug-resistant and oxacillin-resistant *S. aureus* (ORSA). More particularly, MRSA is resistant to a large group of antibiotics called the beta-lactams, which include the penicillins, cephalosporins, and carbapenems. Many strains are also resistant to fluoroquinolones. Vancomycin remains one of only two antimicrobial agents approved by the US Food and Drug Administration (FDA) for treatment of MRSA pneumonia, but its clinical failure rates exceed 30% (4). Explanations for poor therapeutic outcomes include slow, time-dependent bactericidal activity; inadequate dosing; poor penetration into lung tissue and alveolar macrophages (5-11); and reduced susceptibility (4, 12, 13). *S. aureus* is an intracellular and extracellular pathogen (14, 15) that can survive with phagocytes and evade the immune system (16, 17).

Liposome-encapsulation of antimicrobials potentially offers enhanced pharmacokinetics, pharmacodynamics, and decreased toxicity over standard formulations (18, 19). Accumulating higher antimicrobial concentrations in infected tissues would allow for increased uptake by activated tissue macrophages (20, 21), and presumably improve treatment efficacy. Building on that concept, it has been shown that the attachment of polyethylene glycol (PEG) molecules to the surfaces of liposomes effectively delivers the chemotherapeutic drug, gemcitabine, to pancreatic cancer tumor cells. (Cosco D, et al., *Cancer Chemotherapy and Pharmacology*, 64:(5)1009-1020 (2009). The encapsulation of antimicrobials with PEGylated liposomes for use in formulations to treat or prevent bacterial infections, however, has never been described. Indeed, potent antibiotics like vancomycin are often relied upon as a last resort for the treatment of bacteria that are resistant to commonly used antibiotics (e.g., MRSA). However, the effectiveness of vancomycin is reduced by the fact that it poorly penetrates lung tissue. Such problems are commonly experienced during the treatment of MRSA infections of the lungs. Therefore, this invention employs surface PEGylated liposome-encapsulation to more effectively deliver the 'drug-to-bug' by depositing a higher concentration of vancomycin into lung tissue as compared to standard vancomycin formulation.

SUMMARY OF THE INVENTION

This invention is directed to a novel method of treating an individual suffering from a bacterial infection, such as bacterial infections of various tissues or organs of an individual. In general, the method of treatment involves administering to an individual a pharmaceutical formulation that comprises a liposome-encapsulated antimicrobial agent, wherein polyethylene glycol (PEG) molecules are covalently attached to the surface of the liposomes. Thus, the invention relates to PEGylated liposomes that encapsulate a drug, or combination of drugs that are either bactericidal or bacteriostatic.

Generally, the method of treatment of the invention targets gram-positive bacteria. Accordingly, PEGylated liposomes of the invention may, for example, contain antimicrobial agents that are bactericidal or bacteriostatic against methicillin resistant *Staphylococcus aureus* (MRSA), MRSA substrains, and generally other bacteria that are resistant to beta-lactam antibiotics, e.g., the penicillins (dicloxacillin, nafcillin, oxacillin, etc.) and the cephalosporins. The glycopeptide class of antibiotics is particularly well-known in the art as being therapeutically effective against MRSA. Therefore, particular embodiments of the invention relate to PEGylated liposome-encapsulated glycopeptides antibiotics, or combinations of glycopeptides antibiotics, or their derivatives. A glycopeptide antibiotic that is frequently used by clinicians to treated MRSA infections is vancomycin. Accordingly, an embodiment of the invention relates to PEGylated liposome-encapsulated vancomycin or vancomycin derivatives.

Another general objective of the invention is to offer a pharmaceutical formulation that can evade uptake by phagocytic cells, such as macrophages. Therefore, the invention also relates to novel method of delivering antibiotics to infected tissues and organs by encapsulating an antimicrobial agent in PEGylated liposomes that have stealth characteristics with respect to their ability to at least in part avoid cellular clearance mechanisms.

BRIEF DESCRIPTION OF THE TABLES

TABLE 1 contains the main pharmacokinetic parameters of vancomycin in plasma after intravenous administration of 5-mg/kg dose of standard, conventional, and PEGylated liposomal vancomycin formulations.

TABLE 2 contains bio-distribution data for the presence of vancomycin in liver, kidneys, lungs and spleen, after intravenous administration of 5 mg/kg dose of standard, conventional, and PEGylated liposomal vancomycin formulations.

DETAILED DESCRIPTION OF THE INVENTION

Figure 1:
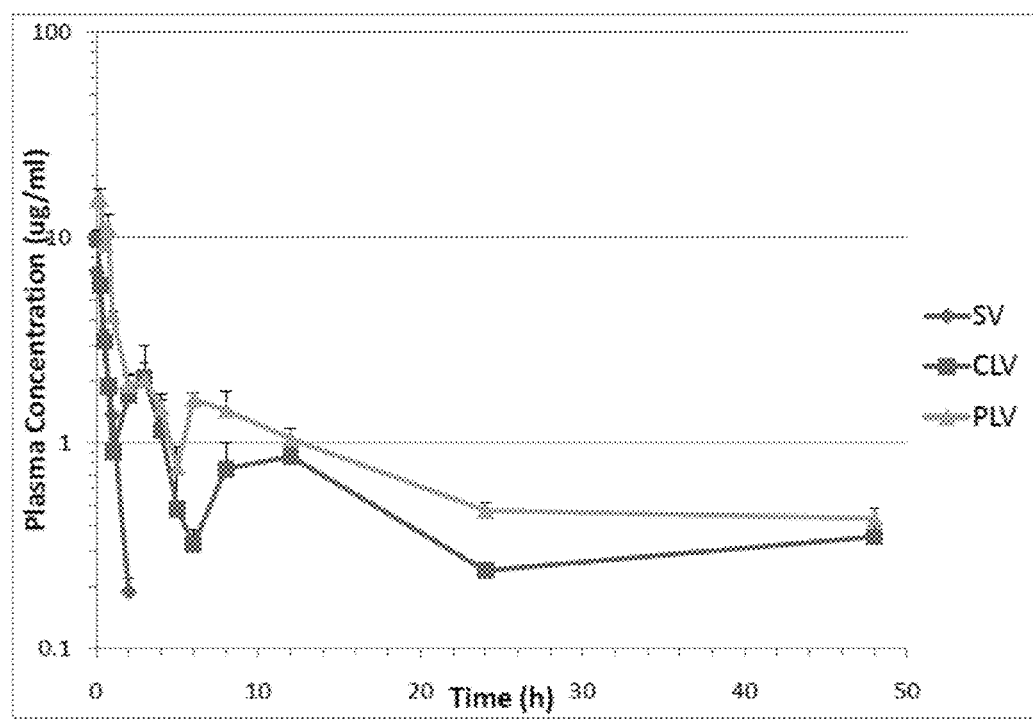
FIG. 1. Pharmacokinetics of vancomycin following intravenous administration of a 5-mg/kg dose of standard vancomycin solution (SV), conventional liposomal vancomycin (CLV), and PEGylated liposomal vancomycin (PLV) in mice. All values are reported as mean±SD.

As described above, the invention is directed to a pharmaceutical formulation comprising an antimicrobial agent, wherein the antimicrobial agent is encapsulated in a liposome, and wherein at least one polyethylene glycol (PEG) molecule is covalently attached to a lipid molecule of the liposome.

With respect to the antimicrobial agent component of the invention, it may exert bactericidal or bacteriostatic activity. In various embodiments of the invention, the pharmaceutical formulation may comprise more than one antimicrobial agent, for example, the formulation may comprise a combination of bacteriostatic and bactericidal antimicrobial agents. Generally, to exert bactericidal activity against bacteria means an antimicrobial agent has the ability of the composition to kill, or irrevocably damage one or more species of bacteria susceptible to the antibiotic of the composition. An antimicrobial agent with bacteriostatic activity, however, has the ability to inhibit the growth of one or more species of bacteria, without death of the one or more target bacterial species susceptible to the antibiotic of the composition. In preferred embodiments of the invention, the antimicrobial agent of the pharmaceutical formulation is bactericidal or bacteriostatic against gram-positive bacteria, including, but not limited to methicillin-resistant *Staphylococcus aureus* (MRSA) bacteria.

In various embodiments of the invention, the antimicrobial agent of the pharmaceutical formulation of the invention is a glycopeptides antibiotic. The term "glycopeptide antibiotic" as used in the context of the invention, and as known to those skilled in the art, refers to an antibiotic with a mechanism of action comprising inhibiting bacterial cell wall growth. Antibiotics in this class of glycopeptide antibiotics include, but are not limited to vancomycin, avoparcin, ristocetin, teicoplanin, and their derivatives. For example, derivatives of vancomycin include, but are not limited to, multivalent vancomycins, PEGylated vancomycin conjugates, norvancomycin, vancomycin disulfides, synmonicin, mono- or di-dechlorovancomycin, glutamine analogs of vancomycin (e.g., A51568B, and M43G), aspartic acid analogs of vancomycin (e.g., M43F, M43B), desvancosamine derivatives of vancomycin (e.g., A51568A and M43A, and corresponding aglycones), chlorine derivatives of vancomycin (e.g., A82846B, A82846A (eremomycin), orienticin A, A82846C), benzylic amino sugar derivatives of vancomycin (e.g., A82846B), N-acyl vancomycins, N-aracyl vancomycins, N-alkyl vancomycins (including but not limited to octylbenzyl, octyloxybenzyl, butylbenzyl, butyloxybenzyl, and butyl, derivatives), or mixtures thereof. In various preferred embodiments of the invention, the pharmaceutical formulation comprises vancomycin, or a derivative of vancomycin, or a combination of vancomycin derivatives.

With regard to the liposome component of the pharmaceutical formulation of the invention, the term "liposome" refers to any lipid composition that can be used to deliver a compound, wherein an aqueous volume is encapsulated by an amphipathic lipid bilayer, or wherein the lipids coat an interior comprising an antimicrobial agent, or combination of antimicrobial agents. Liposomes may be unilamellar, composed of a single bilayer, or they may be multilamellar, composed of two or more concentric bilayers. A phospholipid bilayer is formed from two layers of phospholipid molecules.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, known as a phospholipid bilayer or a lamella, converge into a sphere and in doing so entrap some of the aqueous medium, and whatever may be dissolved or suspended in it, in the core of the sphere, such as, the antimicrobial agent that the pharmaceutical formulation of the invention comprises. For example, in various embodiments of the invention, the pharmaceutical formulation of the invention comprises PEGylated liposomes that have entrapped a solution of vancomycin.

Examples of phospholipids that may be used to create PEGylated liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)]sodium salt, 1,2-dimyristoyl-sn-glycero-3-[phospho-L-serine]sodium salt, 1,2-dioleoyl-sn-glycero-3-phosphoethanolamine-N-glutaryl sodium salt and 1,1',2,2'-tetramyristoyl cardiolipin ammonium salt, or mixtures thereof.

As discussed above, the liposomes of the pharmaceutical formulation that encapsulate the antimicrobial agent have PEG molecules attached to their surfaces. Generally, PEG refers to a polyethylene glycol, a linear, water-soluble polymer of ethylene PEG repeating units with two terminal hydroxyl groups. PEGs are classified by their molecular weights; for example, PEG 2000 has an average molecular weight of about 2,000 Daltons, and PEG 5000 has an average molecular weight of about 5,000 Daltons. PEGs are commercially available from Sigma Chemical Co., Genzyme Pharmaceuticals, and other companies and include, for example, the following: methylpolyethyleneglycol-1,2-distearoylphosphatidyl ethanolamine conjugate (MPEG-2000-DSPE); monomethoxypolyethylene glycol (MPEG-OH), monomethoxypolyethylene glycol-succinate (MPEG-S), monomethoxypolyethylene glycol-succinimidyl succinate (MPEG-S-NHS), monomethoxypolyethylene glycol-amine (MPEG-NH$_2$), monomethoxypolyethylene glycol-tresylate (MPEG-TRES), and monomethoxypolyethylene glycol-imidazolyl-carbonyl (MPEG-IM), or mixtures thereof.

In various embodiments, the PEG is a polyethylene glycol with an average molecular weight of about 550 to about 10,000 Daltons and is optionally substituted by alkyl, alkoxy, acyl or aryl. In an embodiment, the PEG is substituted with methyl at the terminal hydroxyl position. In another embodiment, the PEG has an average molecular weight of about 750 to about 5,000 Daltons, more preferably, of about 1,000 to about 5,000 Daltons, more preferably about 1,500 to about 3,000 Daltons and, even more preferably, of about 2,000 Daltons or of about 750 Daltons. The PEG can be optionally substituted with alkyl, alkoxy, acyl or aryl. In a preferred embodiment, the terminal hydroxyl group is substituted with a methoxy or methyl group. The PEGylated liposomes of the invention may also comprise cholesterol, cholesterol derivatives, or combinations of the derivatives or cholesterol. Generally, the cholesterol component of a PEGylated liposome provides additional stability to the liposome structure. (22)

Within the context of the invention, the molar ratio of phospholipid to cholesterol or cholesterol derivative to PEG may range from 0.1:0.1:0 to 30:10:2. For example, in certain embodiments of the invention, PEGylated liposomes comprise DSPC, cholesterol, and MPEG-2000-DSPE, respectively, is 3:1:0.02.

As stated above, liposomes may be unilamellar, composed of a single bilayer, multilamellar, composed of two or more concentric bilayers. Liposomes range from about 20 nm-100 nm diameter for small unilamellar vesicles (SUVs), about 100 nm-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multilamellar vesicles. During this process some of the aqueous medium is entrapped in the vesicle.

Liposomes can be prepared by any method that is generally known by one of ordinary skill in the art. Examples of commonly used methods of liposome preparation that can be use to prepare the liposomes of the invention include, but are not limited to the dehydration-rehydration, ammonium sulfate gradient, and thin film hydration methods. In various embodiments of the invention, the dehydration-rehydration method used to prepare liposomes is modified.

As discussed above, the pharmaceutical formulation of the invention can be used in the treatment of bacterial infections. Similarly, the pharmaceutical formulation of the invention can be used for the prophylactic treatment of bacterial infections. Thus, the invention therefore includes within its scope pharmaceutical compositions comprising at least one PEGylated liposome-encapsulated antimicrobial agent formulated for use in human or veterinary medicine. Accordingly, such compositions may be presented for use with physiologically acceptable carriers or excipients, optionally with supplementary medicinal agents. Conventional carriers can also be used with the formulation of the invention. The term "treatment" or "treating" within the context of treating a bacterial infection means any treatment of any mammalian tissue that contains at least one bacterium that is not part of the normal flora and fauna of the mammal, or treatment of a mammalian tissue that is infected with bacterial infection in a mammal.

The PEGylated liposome-encapsulated antimicrobial according to the invention can be administered to patients parenterally or orally. Parenteral administrations include intravenous administration, intramuscular administration, subcutaneous administration, rectal administration, or percutaneous administration. Further, the PEGylated liposome encapsulated antimicrobial according to the invention may be formulated into a suitable dosage form depending upon the administration route. Examples of such dosage forms include, for example, injections used mainly, for example, for intravenous administration and intramuscular administration; external preparations for alternate parenteral administration, for example, eye drops, ear drops, nasal drops, ophthalmic ointments, skin mucosa absorbers, dermatologic preparations, inhalants, or suppositories; and preparations for oral administration, for example, capsules, tablets, pills, fine subtilaes, granules, powders, syrups, or troches.

As used herein, the phrase "therapeutically effective amount" shall mean the drug dosage that provides the specific pharmacological response for which the drug is administered in a significant number of subjects in need of such treatment. The actual effective amounts of compound or drug can vary according to the specific composition being utilized, the mode of administration and the age, weight and condition of the patient. For example, as used herein, an effective amount of the drug is an amount which stimulates anti-microbial peptide production. Dosages for a particular individual patient can be determined by one of ordinary skill in the art using conventional considerations, (e.g. by means of an appropriate, conventional pharmacological protocol).

EXAMPLES

Example 1

Preparation of Liposomal Vancomycin Formulations

Liposomes were prepared using one of three methods: 1) the thin film hydration method (23); 2) the ammonium sulfate gradient method (24); and a modified dehydration-rehydration method (25).

To prepare liposomes by the thin film method, 287 mg of 1,2-distearoyl-sn-glycero-3-phosphocholine (DSPC) (Genzyme Pharmaceuticals, Cambridge, Mass.) and 52 mg of cholesterol (Sigma Chemicals, St. Louis, Mo.) were dissolved in 7 ml of HPLC grade chloroform (EMD Chemicals, Gibbstown, N.J.), and evaporated to a film in a rotary evaporator (Buchi Rotavapor R-200, Switzerland). The film was stored overnight at room temperature in a vacuum desiccator, thus allowing the formation of a thin layer of lipid film. The thin lipid film was hydrated by adding vancomycin solution (100 mg of vancomycin hydrochloride (Sigma Chemicals, St. Louis, Mo.) dissolved in 10 ml of phosphate buffered saline (PBS) pH 7.4 (Sigma Chemicals, St. Louis, Mo.)) to the flask containing the thin film of lipids, and the mixture was mixed using the rotavapor for 15 min to form liposomes. The liposomes were either sonicated by using probe sonicator for 10 min. (5 cycles of 2 min each). Then the liposomes were extruded under high pressure using 0.8 µm polycarbonate filter followed by 0.4 µm and 0.2 µm filters. The liposomes were lyophilized for 48 h using suitable amount of sucrose as the cryoprotectant.

PEGylated liposomes were prepared according to the thin film method according to the foregoing method except that 281 mg of DSPC was used, and 6 mg of MPEG-2000-DSPE was included with the initial mixture of DSPC and cholesterol.

Particle size of the liposomes and PEGylated liposomes was measured by using dynamic light scattering technique (NICOMP Model 370 submicron particle sizer, Santa Barbara, Calif.). The liposomal suspension was diluted suitably and particle size was recorded. The mean particle size of conventional liposomes was 254±147 nm and that of PEGylated liposomes was 245±139 nm. The encapsulation efficiency of conventional liposomes was 9±2% and that of PEGylated liposomes was 13±3%.

To separate the unencapsulated drug from liposomes and PEGylated liposomes, a Centrifree® ultrafiltration technique was used. Briefly, 0.4 ml liposomes were added to Centrifree® tubes and centrifuged at 6000 rpm, 25° C. for 15 min using a Beckman ultracentrifuge. The filtrate was analyzed spectrophotometrically at 280 nm after suitable dilutions.

Both conventional and PEGylated liposomal vancomycin formulations were prepared using DSPC, cholesterol and PEG in 3:1:0 and 3:1:0.02 molar ratios, respectively. The detailed procedure for the preparation of liposomal vancomycin formulations has been published recently.

To prepare liposomes by the ammonium sulfate pH gradient method, 143.5 mg of DSPC and 26 mg of cholesterol were dissolved in 5 ml of chloroform, and the solution was evaporated to a film by using a rotary evaporator. The film was stored overnight at room temperature in a vacuum desiccator, thus allowing the formation of a thin layer of lipid film. The film was suspended in 10 ml of 250 mM ammonium sulfate solution for 30 min, and then subjected to 10 cycles of freezing (10 min at −80° C.) and thawing (using a 40° C. water bath). The resultant multilamellar vesicles were extruded five times through a polycarbonate filter (pore size; 200, 100, and 80 nm, Whatman, USA) with a high pressure extruder (Northern Lipids Inc., USA). Particle size was measured by using the dynamic light scattering technique described above. Un-entrapped ammonium sulfate was removed by centrifugation at 4000 rpm for 15 min.

To load the liposomes with vancomycin, the small unilamellar vesicles obtained after centrifugation were suspended in 5 ml of vancomycin solution (50 mg of vancomycin dissolved in 5 ml of PBS pH 7.4) and the resulting solution was allowed to stay at room temperature for 3 h. To separate the liposomes from unencapsulated vancomycin, the liposomes were then passed through a 100 ml sepharose-4B column, and different fractions were collected and the liposomal fractions were pooled. The fractions were analyzed spectrophotometrically at 280 nm after suitable dilutions in order to determine the efficiency of vancomycin encapsulations. The pooled liposomal fractions were then subjected to lyophilization after adding suitable amount (130 mg) of sucrose as the cryoprotectant.

PEGylated liposomes were prepared according to the ammonium sulfate pH gradient method as described above, except that 3 mg of MPEG-2000-DSPE was included with the initial mixture of DSPC and cholesterol, and the vancomycin solution was prepared by adding 50 mg of vancomycin to 2 ml of PBS, rather than to 5 ml.

To prepare liposomes by a modified dehydration-rehydration method, 287 mg of DSPC and 52 mg of cholesterol were dissolved in 7 ml of chloroform, and evaporated to a film in a rotary evaporator. The film was stored overnight at room temperature in a vacuum desiccator, thus allowing the formation of a thin layer of lipid film. The thin lipid film was hydrated by adding 5 ml of high purity, deionized water for 30 min, and sonicated using a probe sonicator for 2 min. The liposomes were lyophilized for 48 h using 140 mg of sucrose as the cryoprotectant.

The liposomes were loaded with vancomycin by adding 1 ml of vancomycin solution (50 mg of vancomycin in 5 ml of PBS, pH 7.0) to the lyophilized empty liposomes, vortexed, and allowed to stay at room temperature for 30 min. The gel produced was then diluted with 4 ml of PBS. The vesicles that formed were subjected to extrusion using 0.8, 0.4 and 0.2 µm filters.

PEGylated liposomes were prepared according to the dehydration-rehydration method according to the foregoing method except that 281 mg of DSPC was used, and 6 mg of MPEG-20000-DSPE was included with the initial mixture of DSPC and cholesterol. Both conventional and PEGylated liposomal vancomycin formulations were prepared using DSPC, cholesterol and PEG in 3:1:0 and 3:1:0.02 molar ratios, respectively.

The vancomycin-loaded liposomes were stored at 4° C. until use. The concentration of vancomycin in the liposomes was measured by using UV-vis spectrophotometry at 497 nm (UV-mini, Shimadzu, Japan) and the loading efficiency was calculated according to the following equation: loading efficiency (%)=$F_t/F_i \times 100$, where $F_t$ is the concentration of vancomycin in the liposomes after their dissolution in organic solvent mixture consisting of chloroform:methanol:distilled water (2:1:0.05, v/v) and $F_i$ is the initial concentration of vancomycin.

Example 2

Pharmacokinetics

Groups of at least 52 mice (Male CF-1 mice from Charles River Lab, Wilmington, Mass.) each received a tail vein injection of a single dose of 5 mg/kg of vancomycin prepared either as a standard vancomycin solution, a conventional formulation of liposome-encapsulated vancomycin, or a formulation of PEGylated liposome-encapsulated vancomycin, respectively. Following the drug administrations, three mice from each different vancomycin formulation group (vancomycin solution, conventional liposome, and PEGylated liposome) were sacrificed by isoflurane (Piramal Health Care, Ltd., AP, India) inhalation at predetermined time points (5, 15, 30 and 45 min, 1, 2, 3, 4, 5, 6, 8, 12, 24 and 48 h). Blood was collected from the sacrificed mice at every time point. Liver, kidney, spleen, lung, and muscle tissues were collected at 1, 4, and 24 h.

Blood samples were placed in heparinized micro-centrifuge tubes, and plasma was separated by centrifugation. A simple protein precipitation procedure was used to extract vancomycin from each plasma sample. More specifically, 200 µl of plasma, 250 µl of acetonitrile, and 250 µl of methanol were added together. The mixture was vortexed for 1 min, and centrifuged at 14,000 rpm for 10 minutes. Four-hundred µl of the supernatant was transferred into a new tube and evaporated to dryness by a stream of filtered air for 1-2 h. The residue that formed in the tube during the evaporation step was reconstituted with 200 µl of high purity, deionized water.

A sensitive, rapid and accurate HPLC method to measure the concentration of vancomycin in a 20 µl sample of each of the reconstituted tissue protein preparation solutions described above was developed and validated. Briefly, chromatographic separation was performed on a VYDAC® C18 column (4.6×50 mm, 3 min) at a detection wavelength of 214 nm. Norvancomycin (10 µl of a 100 µg/ml of norvancomycin (Northern China Pharmaceutical Corp. Shijiazhuang, Hebei, China) was added to 200 µl of plasma and prepared and analyzed in the same manner as the samples). The mobile phases were composed of 0.1% (v/v) TFA as mobile phase A and 95:5 (v/v) acetonitrile/0.1% TFA as mobile phase B, programmed for a 15 min gradient elution where the mobile phase B stayed at 15% for 8 min and linearly increased to 100% over the next 7 min, with a total flow rate of 1 mL/min. Good linearity of the method was achieved over the range 0.1-20 µg/ml. The method was validated according to the International Conference on Harmonization guidelines for validation of analytical procedures with respect to precision, accuracy and linearity. HPLC analysis of vancomycin concentrations in the tissue-derived samples was performed by using a validated HPLC assay to determine the levels of vancomycin. The standard calibration curve was linear in the concentration range of 0.1-20 µg/ml, with a correlation coefficient ($r^2$) higher than 0.995. The lower limit of detection (LLOD, S/N 5) of vancomycin was 0.05 µg/ml, and the lower limit of quantitation (LLOQ, S/N 10) was 0.1 µg/ml. The coefficients of variance ranged from 1.7 to 9.5% for intra-day and 6.3 to 9.4% for inter-day precision.

The pharmacokinetic profiles of all three formulations are shown in FIG. 1. Vancomycin plasma concentrations rapidly declined within the first 2 h of injection of standard vancomycin formulation ($t_{1/2}$~22 min) and after 2 h, no measurable amount could be found. However, following injection of conventional and PEGylated liposomal formulations, plasma vancomycin concentrations remained >1 µg/ml until 4 h and 12 h, respectively. After 48 h, vancomycin was still detectable in plasma.

Pharmacokinetic parameters were calculated using a non-compartmental method, and are reported in Table 1. Table 1 shows that the peak vancomycin plasma concentrations ($C_{max}$) at 5 min were 6.76±0.42 µg/mL and 9.80±1.07 µg/ml for standard and conventional liposomal formulations, respectively; and 15.48±1.71 µg/mL at 15 min for the PEGylated liposomal formulation. The area under the vancomycin plasma concentration-time curve (AUC) was calculated using the linear trapezoidal method. The AUC of conventional liposomes was 4-fold higher than the standard vancomycin, and the AUC of the PEGylated liposomes was 1.7-fold further higher than that of conventional liposomes. The plasma half-life of vancomycin was prolonged when administered as liposomal formulations compared to standard vancomycin. Total body clearance (CL) was calculated as Dose/AUC. Clearance from plasma was decreased by liposomal encapsulation of vancomycin. Because plasma concentrations were determined from samples that included both released and still encapsulated liposomal vancomycin, it is difficult to fit the data into a specific compartmental model and it is not possible to accurately determine all the pharmacokinetic parameters. Data are shown as mean±SD. A two-way ANOVA followed by a Bonferroni post hoc analysis using Graphpad® Prism software (La Jolla, Calif., USA) was performed to determine statistical significance. P value of ≤0.05 was considered significant.

TABLE 1

| Vancomycin Formulation | $C_{max}$ (µg/ml) | $AUC_{0-48}$ (µg·h/ml) | CL (ml/h) |
|---|---|---|---|
| Standard Solution | 6.76 ± 0.42 | 6.82 ± 0.18 | 1.83 ± 0.25 |
| Conventional Liposomes | 9.79 ± 1.07 | 25.91 ± 2.82 | 0.48 ± 0.26 |
| PEGylated Liposomes | 15.48 ± 1.71 | 47.19 ± 0.72 | 0.26 ± 0.23 |

Example 3

Bio-Distribution

The bio-distribution of vancomycin into the liver, kidneys, lungs, spleen, and muscle following administration of a single intravenous dose of 5-mg/kg of standard, conventional, and PEGylated liposomal vancomycin formulations was determined. The administrations of the foregoing formulations to the respective groups of mice, and the post-administration sacrifice schedule, were performed as described by Example 2. Tissues were prepared and analyzed according to the following protocols.

As explained above, several major organs (liver, kidney, lung, spleen, and muscle) were analyzed to determine the distribution of vancomycin in these tissues 1, 4, and 24 h after intravenous administration of vancomycin prepared either as a standard vancomycin solution, a conventional formulation of liposome-encapsulated vancomycin, or a formulation of PEGylated liposome-encapsulated vancomycin, respectively. Tissue samples were weighed and homogenized in PBS (0.5 mg/ml for liver, kidneys, lungs, and muscle; and 0.2 mg/ml for spleen). After homogenization, 300 µl of the homogenate was transferred into a 1.5 ml Eppendorf micro-centrifuge tube, to which 250 µl of acetonitrile and 250 µl of methanol were added. The mixture was subsequently vortexed for 1 min, and centrifuged at 14,000 rpm for 10 min. Five-hundred µl of supernatant was transferred into a test tube and evaporated by a stream of filtered air for 1-2 h. The residue that formed in the tube during the evaporation step was reconstituted with 200 µl of high purity, deionized water. For use as an internal control standard, 10 µl of a 100 µg/ml solution of norvancomycin was added to each tube and the mixture was vortexed for 1 minute, and prepared and analyzed in exactly the same manner as the samples. HPLC analysis of vancomycin concentrations in the tissue-derived samples was performed by using a method similar to the one described above. The HPLC results are reported directly below.

Figure 2:
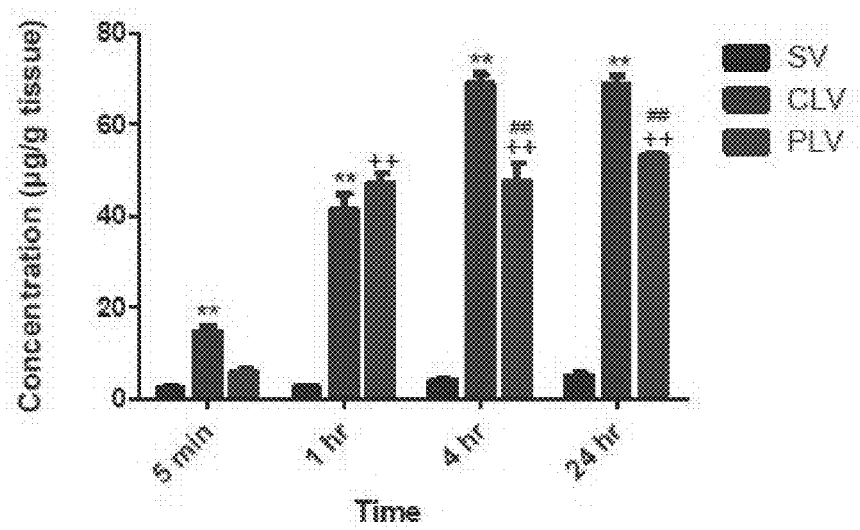
FIG. 2. Tissue distribution of total vancomycin in the spleen of CF-1 mice following intravenous administration of a 5 mg/kg dose of standard vancomycin solution (SV), conventional liposomal vancomycin (CLV), and PEGylated liposomal vancomycin (PLV). **P<0.001 conventional liposomes vs. standard vancomycin at 5 min. ++P<0.001 PEGylated liposomes vs. standard vancomycin at 5 min. *P<0.01 conventional liposomes vs. standard vancomycin at 1 hr. +P<0.01 PEGylated liposomes vs. standard vancomycin at 1 hr.
Figure 3:
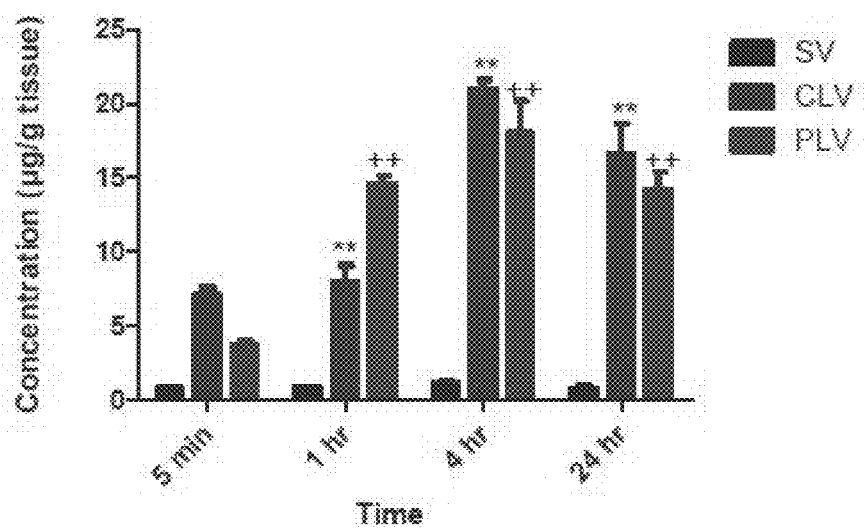
FIG. 3. Tissue distribution of vancomycin in the liver of male CF-1 mice following intravenous administration of a 5-mg/kg dose of standard vancomycin solution (SV), conventional liposomal vancomycin (CLV), and PEGylated liposomal vancomycin (PLV). **P<0.001 conventional liposomes vs. standard vancomycin at 5 min. ++P<0.001 PEGylated liposomes vs. standard vancomycin at 5 min. *P<0.01 conventional liposomes vs. standard vancomycin at 1 hr. +P<0.01 PEGylated liposomes vs. standard vancomycin at 1 hr.

Liposome-encapsulation enhanced reticuloendothelial system uptake as evidenced by increased levels of vancomycin in the spleen and liver tissues (See FIG. 2 and FIG. 3). Uptake of vancomycin by the spleen from the PEGylated liposomes at 4 h and 24 h was significantly less than the vancomycin from conventional liposomes, (P<0.001, FIG. 2), and uptake of vancomycin by the liver from conventional and PEGylated liposomal formulations into liver tissue was significantly greater than from standard vancomycin at 1, 4, and 24 h (P<0.001, FIG. 3). Maximum concentration of vancomycin in the liver occurred 4 h after the administration of the drug, regardless of which vancomycin formulation was administered. AUC, AUMC, and MRT values are presented in Table 2.

Figure 4:
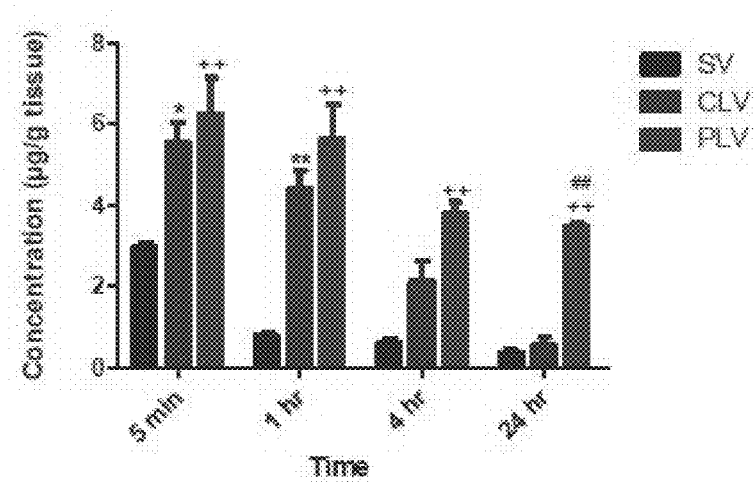
FIG. 4. Tissue distribution of vancomycin in the lungs of CF-1 mice following intravenous administration of a 5-mg/kg dose of standard vancomycin solution (SV), conventional liposomal vancomycin (CLV), and PEGylated liposomal vancomycin (PLV). **P<0.001 conventional liposomes vs. standard vancomycin at 5 min. ++P<0.001 PEGylated liposomes vs. standard vancomycin at 5 min. *P<0.01 conventional liposomes vs. standard vancomycin at 1 hr. +P<0.01 PEGylated liposomes vs. standard vancomycin at 1 hr.

With respect to distribution of vancomycin to the lung, vancomycin encapsulated in conventional or PEGylated liposomes was associated with greater distribution of vancomycin into lung tissue than was the standard solution of vancomycin (FIG. 4). Furthermore, the distribution of vancomycin at 5 min, 1 h, 4 h, and 24 h following the administration of PEGylated liposome-encapsulated vancomycin was greater than the distribution of vancomycin following the administration of conventional liposome-encapsulated vancomycin. The difference at 24 h was statistically significant ($P<0.001$, FIG. 4). AUC, AUMC, and MRT values are presented in Table 2.

Figure 5:
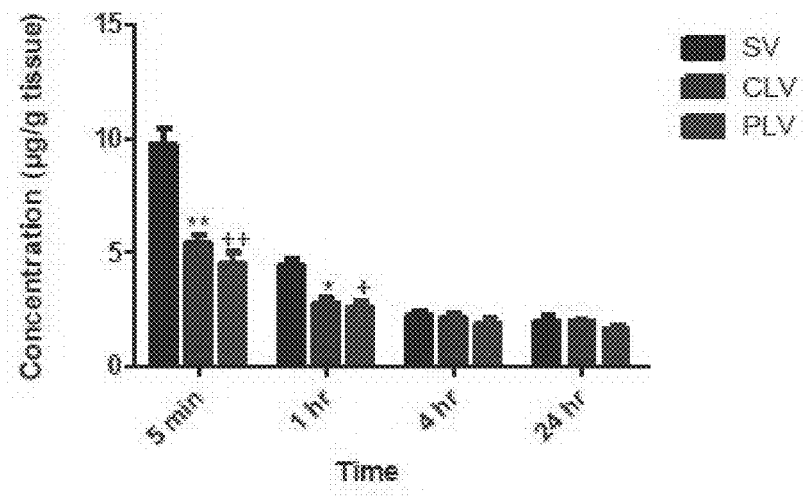
FIG. 5. Tissue distribution of vancomycin in the kidneys of CF-1 mice following intravenous administration of a 5-mg/kg dose of standard vancomycin solution (SV), conventional liposomal vancomycin (CLV), and PEGylated liposomal vancomycin (PLV). **P<0.001 conventional liposomes vs. standard vancomycin at 5 min. ++P<0.001 PEGylated liposomes vs. standard vancomycin at 5 min. *P<0.01 conventional liposomes vs. standard vancomycin at 1 hr. +P<0.01 PEGylated liposomes vs. standard vancomycin at 1 hr.

With respect to distribution of vancomycin to the kidneys, vancomycin encapsulated in liposomes was generally associated with less pronounced distribution as compared to the standard vancomycin solution (FIG. 5). There was a significant difference between the distribution of vancomycin to kidneys that was associated with the two liposomal formulations as compared to the distribution of the standard vancomycin formulation at 5 min ($P<0.001$) and 1 h ($P<0.01$). AUC, AUMC, and MRT values are contained in Table 2.

With respect to distribution of vancomycin to muscle, there were no significant levels of vancomycin were detected in muscle tissue at any of the time points, regardless of which formulation was administered.

TABLE 2

| | Pharmacological Measurement | Standard Solution | Liposome | PEGylated Liposome |
|---|---|---|---|---|
| Liver | AUC | 21.91 ± 5.29 | 426.27 ± 44.32 | 378.91 ± 36.35 |
| | Cmax | 1.09 ± 0.22 | 20.99 ± 1.11 | 18.02 ± 3.76 |
| | MRT | 10.46 ± 1.63 | 11.65 ± 0.86 | 11.22 ± 1.31 |
| Kidneys | AUC | 58.60 ± 5.70 | 51.72 ± 40.05 | 44.55 ± 3.91 |
| | Cmax | 9.76 ± 1.21 | 5.38 ± 0.71 | 4.51 ± 0.88 |
| | MRT | 9.94 ± 0.90 | 11.10 ± 0.77 | 10.71 ± 2.06 |
| Lungs | AUC | 13.46 ± 2.07 | 40.68 ± 13.54 | 92.23 ± 10.08 |
| | Cmax | 2.96 ± 0.21 | 5.52 ± 0.90 | 6.25 ± 1.54 |
| | MRT | 8.82 ± 1.94 | 5.73 ± 1.28 | 11.07 ± 0.63 |
| Spleen | AUC | 99.39 ± 18.72 | 1563.08 ± 69.56 | 1169.35 ± 86.33 |
| | Cmax | 4.94 ± 0.99 | 68.79 ± 3.68 | 52.98 ± 1.24 |
| | MRT | 13.75 ± 0.48 | 12.59 ± 0.35 | 12.82 ± 0.54 |

REFERENCES

1. Rubinstein E, Kollef M H, Nathwani D. *Pneumonia caused by methicillin-resistant Staphylococcus aureus*. Clin Infect Dis. [Article]. 2008 June; 46:S378-S85.
2. *Guidelines for the management of adults with hospital-acquired, ventilator-associated, and healthcare-associated pneumonia*. Am J Respir Crit Care Med. [Review]. 2005 February; 171(4):388-416.
3. Kuehnert M J, Hill H A, Kupronis B A, Tokars J I, Solomon S L, Jernigan D B. *Methicillin resistant-Staphylococcus aureus hospitalizations, United States*. Emerg Infect Dis. [Article]. 2005 June; 11(6):868-72.
4. Choi E Y, Huh J W, Lim C M, Koh Y, Kim S H, Choi S H, et al. *Relationship between the MIC of vancomycin and clinical outcome in patients with MRSA nosocomial pneumonia*. Intensive Care Med. 2011 April; 37(4):639-47.
5. Shulman L M, Pretzer-Aboff I, Anderson K E, Stevenson R, Vaughan C G, Gruber-Baldini A L, et al. *Subjective report versus objective measurement of activities of daily living in Parkinson's disease*. Mov Disord. 2006 June; 21(6):794-9.
6. Kollef M H. *Limitations of vancomycin in the management of resistant staphylococcal infections*. Clin Infect Dis. [Article]. 2007 September; 45:S191-S5.
7. Stevens D L. *The role of vancomycin in the treatment paradigm*. Clin Infect Dis. 2006 Jan. 1; 42 Suppl 1:S51-7.
8. Cruciani M, Gatti G, Lazzarini L, Furlan G, Broccali G, Malena M, et al. *Penetration of vancomycin into human lung tissue*. J Antimicrob Chemother. 1996 Nov. 1, 1996; 38(5):865-9.
9. Moise-Broder P A, Forrest A, Birmingham M C 278, Schentag J J. *Pharmacodynamics of vancomycin and other antimicrobials in patients with Staphylococcus aureus lower respiratory tract infections*. Clin Pharmacokinet. [Review]. 2004; 43(13):925-42.
10. Onyeji C O, Nightingale C H, Marangos M N. *Enhanced killing of methicillin resistant Staphylococcus aureus in human macrophages by liposome-entrapped vancomycin and teicoplanin*. Infection. 1994; 22(5):338-42.
11. Pumerantz A, Muppidi K, Agnihotri S, Guerra C, Venketaraman V, Wang J, et al. *Preparation of liposomal vancomycin and intracellular killing of meticillin-resistant Staphylococcus aureus (MRSA)*. Int J Antimicrob Agents. 2011 February; 37(2):140-4.
12. Gould I M. *Clinical relevance of increasing glycopeptide MICs against Staphylococcus aureus*. Int J Antimicrob Agents. 2008 April; 31 Suppl 2:1-9.
13. Steinkraus G, White R, Friedrich L. *Vancomycin MIC creep in non-vancomycin intermediate Staphylococcus aureus (VISA), vancomycin-susceptible clinical methicillin resistant S. aureus (MRSA) blood isolates from 2001-05*. J Antimicrob Chemother. 2007 October; 60(4):788-94.
14. Lowy F D. *Is Staphylococcus aureus an intracellular pathogen?* Trends Microbiol. [Editorial Material]. 2000 August; 8(8):341-3.
15. Sinha B, Fraunholz M. *Staphylococcus aureus host cell invasion and post-invasion events*. Int J Med Microbiol. [Review]. 2010 February; 300(2-3):170-5.
16. Garzoni C, Kelley W L. *Staphylococcus aureus: new evidence for intracellular persistence*. Trends Microbiol. [Review]. 2009 February; 17(2):59-65.
17. Foster T J. *Immune evasion by Staphylococci*. Nat Rev Microbiol. [Review]. 2005 December; 3(12):948-58.
18. Allen T M. Liposomal drug formulations. *Rationale for development and what we can expect for the future*. Drugs. 1998 November; 56(5):747-56.

19. Drulis-Kawa Z, Dorotkiewicz-Jach A. *Liposomes as delivery systems for antibiotics*. International Journal of Pharmaceutics. 387(1-2):187-98.
20. Bakker-Woudenberg I, Schiffelers R M, Storm G, Becker M J, Guo L. *Long-circulating sterically stabilized liposomes in the treatment of infections*. Liposomes, Pt E. San Diego: Elsevier Academic Press Inc; 2005. p. 228-60.
21. Bakker-Woudenberg I. *Long-circulating sterically stabilized liposomes as carriers of agents for treatment of infection or for imaging infectious foci*. Int J Antimicrob Agents. [Proceedings Paper]. 2002 April; 19(4):299-311.
22. Kirby C, Clarke J, Gregoriadis G. *Effect of the Cholesterol Content of Small Unilamellar Liposomes on their Stability in vivo and in vitro*. Biochem J. 1980 186:591-98.
23. Bangham A D, Standish M M, Watkins J C. *Diffusion of univalent ions across the lamellae of swollen phospholipids*. J Mol Biol. 1965 1965; 13(1):238-52.
24. Jung S H, Seong H, Cho S H, Jeong K S, Shin B C. *Polyethylene glycol-complexed cationic liposome for enhanced cellular uptake and anticancer activity*. International Journal of Pharmaceutics. [Article]. 2009 December; 382(1-2):254-61.
25. Anderson K E, Eliot L A, Stevenson B R, Rogers J A. *Formulation and evaluation of a folic acid receptor-targeted oral vancomycin liposomal dosage form*. Pharm Res. [Article]. 2001 March; 18(3):316-22.

The claimed invention is:

1. A liposome-encapsulated antimicrobial agent, wherein the liposome consists of a (A) phospholipid, (B) cholesterol, and (C) methylpolyethyleneglycol-1,2-distearoylphosphatidyl ethanolamine (DSPE-mPEG) which are present in weight ratios (A:B:C) ranging from (0.8-1.2):(0.16-0.20):(0.018-0.022), and encapsulates an aqueous solution of the antimicrobial agent.

2. A liposome-encapsulated antimicrobial agent according to claim 1, wherein the antimicrobial agent is a glycopeptide antibiotic.

3. A liposome-encapsulated antimicrobial agent according to claim 2, wherein the glycopeptide antibiotic is vancomycin, avoparcin, ristocetin, teicoplanin, a derivative of vancomycin, avoparcin, ristocetin, or teicoplanin.

4. A liposome-encapsulated antimicrobial agent according to claim 3, wherein the derivative of vancomycin is a multivalent vancomycin, vancomycin disulfide, mono- or di-dechlorovancomycin, a glutamine analog of vancomycin, an aspartic acid analog of vancomycin, a desvancosamine derivative of vancomycin, a chlorine derivative of vancomycin, a benzylic amino sugar derivative of vancomycin, N-acyl vancomycin, N-aracyl vancomycins, and N-alkyl vancomycin.

5. A liposome-encapsulated antimicrobial agent according to claim 1, wherein the phospholipid is 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)]sodium salt, 1,2-dimyristoyl-sn-glycero-3-[phospho-L-serine]sodium salt, 1,2-dioleoyl-sn-glycero-3-phosphoethanolamine-N-glutaryl sodium salt, or 1,1',2,2T-tetramyristoyl cardiolipin ammonium salt.

6. A liposome-encapsulated antimicrobial agent according to claim 5, wherein the phospholipid is 1,2-distearoyl-sn-glycero-3-phosphocholine (DSPC).

7. A liposome-encapsulated antimicrobial agent according to claim 1, wherein the weight ratios of (A:B:C) are 1:0.18:0.02.

8. A method of treating a bacterial infection of a tissue or organ of a patient comprising administering to the patient an effective amount of the liposome-encapsulated antimicrobial agent according to claim 1.

9. A method of treating a bacterial infection according to claim 8, wherein the bacterial infection is caused by gram-positive bacteria.

10. A method of treating a bacterial infection according to claim 9, wherein the gram-positive bacteria are Methicillin-resistant *Staphylococcus aureus* (MRSA).

11. A method of treating a bacterial infection according to claim 8 wherein the gram-positive bacteria is in the intracellular compartment of a cell.

12. A method of treating a bacterial infection according to claim 8, wherein the infected tissue or organ is lung, liver, spleen, kidney, or blood.

13. A method of treating a bacterial infection according to claim 12, wherein the infected tissue or organ is lung.

14. A liposome-encapsulated antimicrobial agent according to claim 1, wherein the DSPE-mPEG is DSPE-mPEG (550), a DSPE-mPEG(750), DSPE-mPEG(1000), DSPE-mPEG(2000), DSPE-mPEG(3000), or DSPE-mPEG(5000).

15. A liposome-encapsulated antimicrobial agent according to claim 14, wherein the DSPE-mPEG is DSPE-mPEG (2000).

16. A liposome-encapsulated glycopeptide antibiotic, wherein the liposome comprises: (A) 1,2-distearoyl-sn-glycero-3-phosphocholine (DSPC), (B) cholesterol, and (C) DSPE-mPEG(2000) which are present in weight ratios (A:B:C) ranging from (0.8-1.2):(0.16-0.20):(0.018-0.022), and encapsulates an aqueous solution of the glycopeptide antibiotic.

17. A liposome-encapsulated glycopeptide antibiotic according to claim 16, wherein the glycopeptide antibiotic is vancomycin.

18. A liposome-encapsulated glycopeptide antibiotic according to claim 17, wherein the weight ratios (A:B:C) are 1:0.18:0.02.

19. A liposome-encapsulated glycopeptide antibiotic according to claim 17 or 18, wherein the aqueous solution of vancomycin comprises 10 mg/ml vancomycin.

* * * * *